United States Patent
Mikos et al.

(10) Patent No.: US 6,689,608 B1
(45) Date of Patent: *Feb. 10, 2004

(54) POROUS BIODEGRADABLE POLYMERIC MATERIALS FOR CELL TRANSPLANTATION

(75) Inventors: Antonios G. Mikos, Houston, TX (US); Robert S. Langer, Newton, MA (US); Joseph P. Vacanti, Winchester, MA (US); Linda G. Griffith, Cambridge, MA (US); Georgios Sarakinos, Maastricht (NL)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/669,760

(22) Filed: Sep. 26, 2000

Related U.S. Application Data

(63) Continuation of application No. 08/052,387, filed on Apr. 23, 1993, now abandoned, which is a continuation-in-part of application No. 08/012,270, filed on Feb. 1, 1993, now Pat. No. 5,514,378.

(51) Int. Cl.$^7$ .............................. C12N 5/06; C12N 5/08; C12N 11/08; A61F 2/00
(52) U.S. Cl. ...................... 435/395; 424/426; 424/93.7; 435/180
(58) Field of Search ................. 435/174, 177, 435/180, 182, 395; 424/93.7, 423, 426

(56) References Cited

U.S. PATENT DOCUMENTS

| | | | |
|---|---|---|---|
| 4,060,081 A | 11/1977 | Yannas et al. | 128/156 |
| 4,186,448 A * | 2/1980 | Brekke | 3/1.9 |
| 4,352,883 A | 10/1982 | Lim | 435/178 |
| 4,391,909 A | 7/1983 | Lim | 435/178 |
| 4,458,678 A | 7/1984 | Yannas et al. | 128/155 |
| 4,485,097 A | 11/1984 | Bell | 424/95 |
| 4,520,821 A | 6/1985 | Schmidt et al. | |
| 4,563,489 A | 1/1986 | Urist | 524/21 |
| 4,846,835 A | 7/1989 | Grande | 623/11 |
| 4,897,267 A | 1/1990 | Bontempts et al. | 424/426 |
| 5,041,138 A | 8/1991 | Vacanti et al. | 623/16 |
| 5,064,866 A | 11/1991 | Toyomoto et al. | 521/27 |
| 5,096,814 A | 3/1992 | Aivasidis et al. | 435/41 |
| 5,514,378 A | 5/1996 | Mikos et al. | 424/425 |
| 5,567,612 A * | 10/1996 | Vacanti et al. | 424/93.7 X |
| 5,736,372 A * | 4/1998 | Vacanti et al. | 435/180 |
| 5,759,830 A * | 6/1998 | Vacanti et al. | 435/180 |
| 5,770,193 A * | 6/1998 | Vacanti et al. | 424/93.7 |
| 5,804,178 A * | 9/1998 | Vacanti et al. | 424/93.7 |
| 6,309,635 B1 * | 10/2001 | Ingber et al. | 424/93.7 |

FOREIGN PATENT DOCUMENTS

| | | |
|---|---|---|
| CH | 678407 | 9/1991 |
| JP | 1268733 | 1/1989 |
| WO | 9072604 | 11/1990 |

OTHER PUBLICATIONS

Vacanti et al., *Journal of Pediatric Surgery* 23:3–9 (Jan. 98).

* cited by examiner

Primary Examiner—David M. Naff
(74) Attorney, Agent, or Firm—Clark & Elbing LLP; Kristina Bieker-Brady

(57) ABSTRACT

Polymeric materials are used, to make a pliable, non-toxic, injectable porous template for vascular ingrowth. The pore size, usually between approximately 100 and 300 microns, allows vascular and connective tissue ingrowth throughout approximately 10 to 90% of the matrix following implantation, and the injection of cells uniformly throughout the implanted matrix without damage to the cells or patient. The introduced cells attach to the connective tissue within the matrix and are fed by the blood vessels. The preferred material for forming the matrix or support structure is a biocompatible synthetic polymer which degrades in a controlled manner by hydrolysis into harmless metabolites, for example, polyglycolic acid, polylactic acid, polyorthoester, polyanhydride, or copolymers thereof. The rate of tissue ingrowth increases as the porosity and/or the pore size of the implanted devices increases. The time required for the tissue to fill the device depends on the polymer crystallinity and is less for amorphous polymers versus semicrystalline polymers. The vascularity of the advancing tissue is consistent with time and independent of the biomaterial composition and morphology.

7 Claims, 6 Drawing Sheets

5 Days

15 Days

25 Days

35 Days

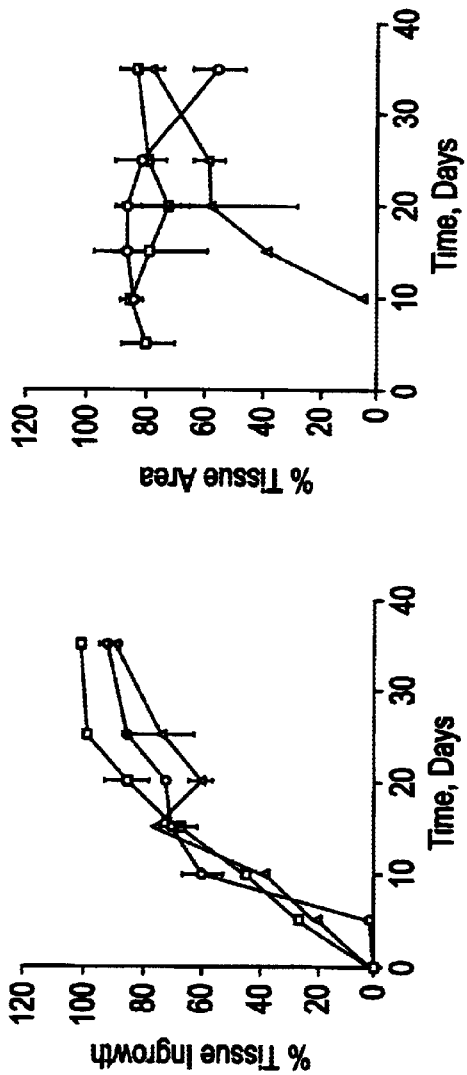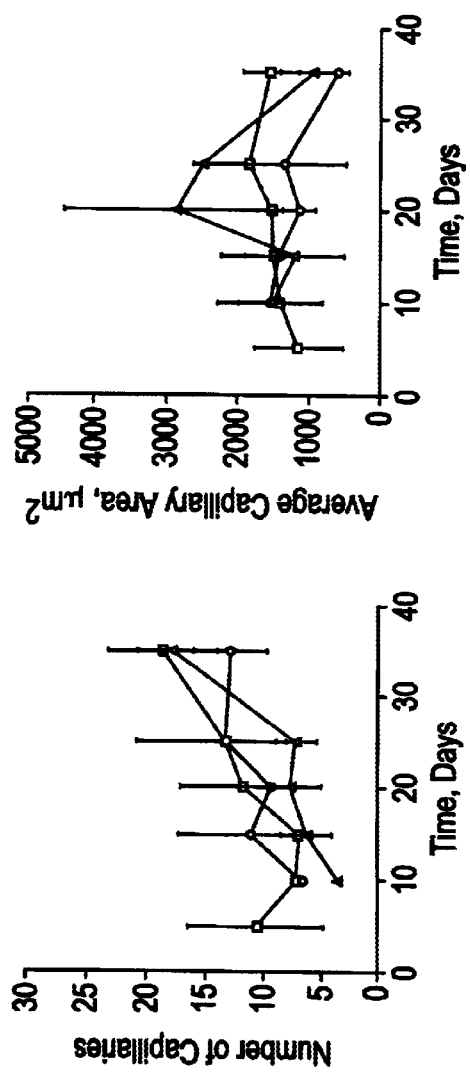

POROUS BIODEGRADABLE POLYMERIC MATERIALS FOR CELL TRANSPLANTATION

This is a continuation of and claims priority from U.S. Ser. No. 08/052,387, filed Apr. 23, 1993, now abandoned, which is a continuation-in-part of U.S. Ser. No. 08/012,270, filed Feb. 1, 1993, now issued as U.S. Pat. No. 5,514,378.

BACKGROUND OF THE INVENTION

This invention is generally in the field of polymeric materials, and in particular in the area of biocompatible artificial matrices for implantation of cells.

Loss of organ function can result from congenital defects, injury or disease. Many times treatment with drugs or surgery is not in itself sufficient and the patient dies or is severely disabled. One approach for treatment has been to transplant donor organs or tissue into the patient. Drugs such as cyclosporin can be used to prevent tissue rejection. However, there is a tremendous shortage of donor organs, most of which must come from a recently deceased individual.

There have been a number of attempts to culture dissociated tissue and implant the cells directly into the body. One of the problems with implanting dissociated cells into the body is that they do not form three dimensional structures and the cells are lost by phagocytosis and attrition. One approach to overcome this problem is described by U.S. Pat. No. 4,352,883 to Lim, wherein cells are encapsulated within alginate microspheres, then implanted. While this method can sometimes maintain viable functioning cells, the cells do not form organs or structures and rarely result in long term survival and replication of the encapsulated cells. Most cells have a requirement for attachment to a surface in order to replicate and to function.

The first attempts to culture cells on a matrix for use as artificial skin, which requires formation of a thin three dimensional structure, were described by Yannas and Bell in a series of publications. They used collagen type structures which were seeded with cells, then placed over the denuded area. A problem with the use of the collagen matrices was that the rate of degradation is not well controlled. Another problem was that cells implanted into the interior of thick pieces of the collagen matrix failed to survive.

One method for forming artificial skin by seeding a fibrous lattice with epidermal cells is described in U.S. Pat. No. 4,485,097 to Bell, which discloses a hydrated collagen lattice that, in combination with contractile agents such as platelets and fibroblasts and cells such as keratinocytes, is used to produce a skin-equivalent. U.S. Pat. No. 4,060,081, to Yannas et al. discloses a multilayer membrane useful as synthetic skin which is formed from an insoluble non-immunogenic material which is nondegradable in the presence of body fluids and enzymes, such as cross-linked composites of collagen and a mucopolysaccharide, overlaid with a non-toxic material such as a synthetic polymer for controlling the moisture flux of the overall membrane. U.S. Pat. No. 4,458,678 to Yannas et al. discloses a process for making a skin-equivalent material wherein a fibrous lattice formed from collagen cross-linked with glycosaminoglycan is seeded with epidermal cells. A disadvantage to the first two materials is that the matrix is formed of a "permanent" synthetic polymer. In the third case, the matrix can be biodegradable but, since it is formed primarily of collagen, only by enzymatic action, which occurs in an uncontrolled manner.

U.S. Pat. No. 4,520,821 to Schmidt describes a similar approach that was used to make linings to repair defects in the urinary tract. Epithelial cells were implanted onto synthetic non-woven biodegradable polymeric matrices, where they formed a new tubular lining as the matrix degraded. The matrix served a two fold purpose—to retain liquid while the cells replicated, and to hold and guide the cells as they replicated. However, this approach is clearly limited to repair or replacement of very thin linings.

Vacanti, et al., *Arch. Surg.* 123, 545–549 (1988), describes a method of culturing dissociated cells on biocompatible, biodegradable matrices for subsequent implantation into the body was described. This method was designed to overcome a major problem with previous attempts to culture cells to form three dimensional structures having a diameter of greater than that of skin. Vacanti and Langer recognized that there was a need to have two elements in any matrix used to form organs: adequate structure and surface area to implant a large volume of cells into the body to replace lost function and a matrix formed in a way that allowed adequate diffusion of gases and nutrients throughout the matrix as the cells attached and grew to maintain viability in the absence of vascularization. Once implanted and vascularized, the porosity required for diffusion of the nutrients and gases was no longer critical.

However, even with the method described by Vacanti, the implant was initially constructed in vitro, then implanted. It is clearly desirable to be able to avoid the in vitro step. It is also desirable to have better ways that can be used to form synthetic, biodegradable matrices that can be implanted and sustain cell growth in vivo, degrading in a controlled manner to leave functional, viable cells organized to form an organ equivalent.

It is therefore an object of the present invention to provide a polymeric material which can be implanted into the body, vascularized and used as a means to achieve a high survival rate for dissociated cells injected into the matrix.

It is a further object of the present invention to provide a biocompatible, polymeric implant which can be implanted with cells without prior in vitro culturing and then degrades at a controlled rate over a period of time as the implanted cells replicate and form an organ structure.

SUMMARY OF THE INVENTION

Polymeric materials are used to make a pliable, non-toxic, implantable porous template for vascular ingrowth and into which cells can be injected. The pore size, usually between approximately 100 and 300 microns, allows vascular and connective tissue ingrowth throughout approximately 10 to 90% of the matrix following implantation, and the injection of cells uniformly throughout the implanted matrix without damage to the cells or patient. The introduced cells attach to the connective tissue within the matrix and are fed by the blood vessels. The preferred material for forming the matrix or support structure is a biocompatible synthetic polymer which degrades in a controlled manner by hydrolysis into harmless metabolites, for example, polyglycolic acid, polylactic acid, polyorthoester, polyanhydride, or copolymers thereof. The elements of these materials can be overlaid with a second material to enhance cell attachment. The polymer matrix is configured to provide access to ingrowing tissues to form adequate sites for attachment of the required number of cells for viability and function and to allow vascularization and diffusion of nutrients to maintain the cells initially implanted.

As described in the examples, highly-porous biocompatible and biodegradable polymers forms were prepared and implanted in the mesentery of rats for a period of 35 days to study the dynamics of tissue ingrowth and the extent of tissue vascularity, and to explore their potential use as substrates for cell transplantation. The advancing fibrovascular tissue was characterized from histological sections of harvested devices by image analysis techniques. The rate of tissue ingrowth increased as the porosity and/or the pore size of the implanted devices increased. The time required for the tissue to fill the device depended on the polymer crystallinity and was less for amorphous polymers versus semicrystalline polymers. The vascularity of the advancing tissue was consistent with time and independent of the biomaterial composition and morphology.

BRIEF DESCRIPTION OF THE DRAWINGS

FIGS. 3a, 3b, 3c, and 3d, are graphs of the normalized tissue ingrowth (FIG. 3a), fraction of tissue area of prevascularized regions (FIG. 3b), number of capillaries per field (FIG. 3c), and average capillary area ($\mu m^2$) (FIG. 3d), as a function of implantation time (days), for semicrystalline PLLA devices of different porosities and pore sizes [L90e (squares); L90c (circles); and L80e (triangles)] implanted in a dry form. The error bars for the tissue ingrowth designate averages±range of two experiments whereas those for the tissue area, the number of capillaries, and the average capillary area stand for averages±standard deviation of three 1×1 mm² fields of the same histological section.

FIG. 6A is a graph showing the relationship between the porosity of the membranes as a function of the initial sodium chloride weight fraction. The open square symbol represents salt having a diameter between 0 and 53 microns. The open circle represents salt having a diameter between 53 and 106 microns. The open triangle represents salt having a diameter between 106 and 150 microns. The black square represents salt having a diameter between 150 and 250 microns. The black circle represents salt having a diameter between 250 and 500 microns. FIG. 6B is a graph showing the relationship between the surface to volume ratio of the membranes and the initial sodium chloride weight fraction.

DETAILED DESCRIPTION OF THE INVENTION

As described in more detail below, the present invention is the preparation and use of synthetic, biocompatible, biodegradable polymeric matrices for implantation into a patient, followed by seeding of cells. In the preferred method, the matrix is implanted, vascularized by ingrowth of capillaries and connective tissue from the recipient, then the cells are seeded.

Methods described herein relate to the manufacture of polymeric membranes having a thickness that is preferably between 500 and 2000 microns, formed of biocompatible, preferably biodegradable, synthetic polymers, which have interconnected interstices with a pore size range between greater than 0 and 500 microns, most preferably for seeking of cells, in excess of 100 to 150 microns.

Figure 6A:
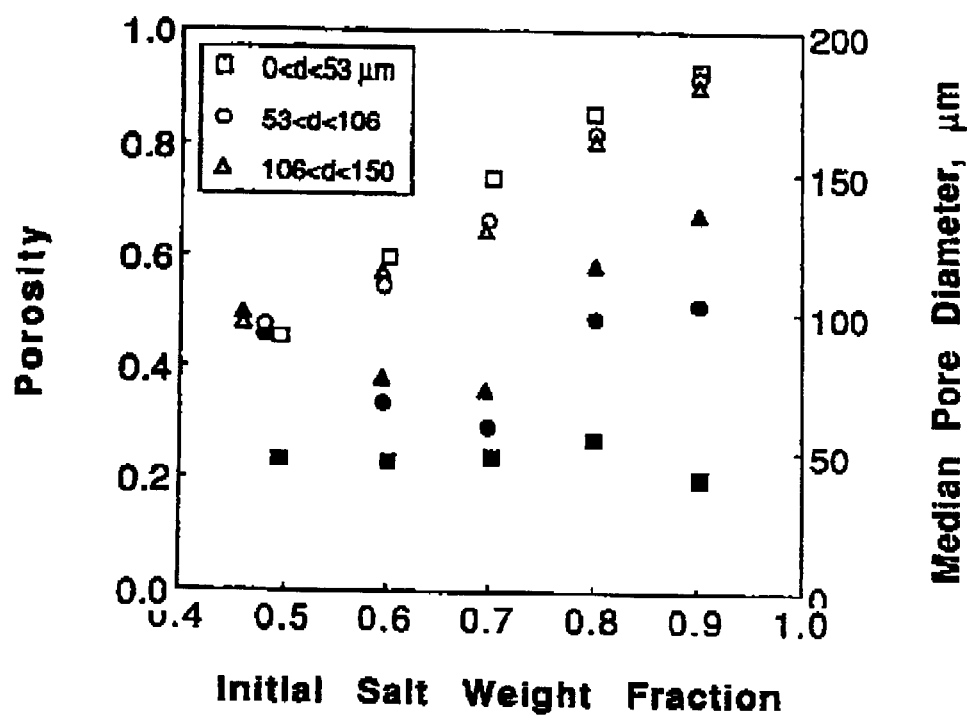
FIGS. 6A and 6B are graphs of the effect of initial salt weight faction and salt particle diameter on the porosity, median pore diameter (microns), and surface/volume ratio (1/micron) of poly(lactic acid) (PLLA) membranes, prepared by the method described herein.
Figure 6B:
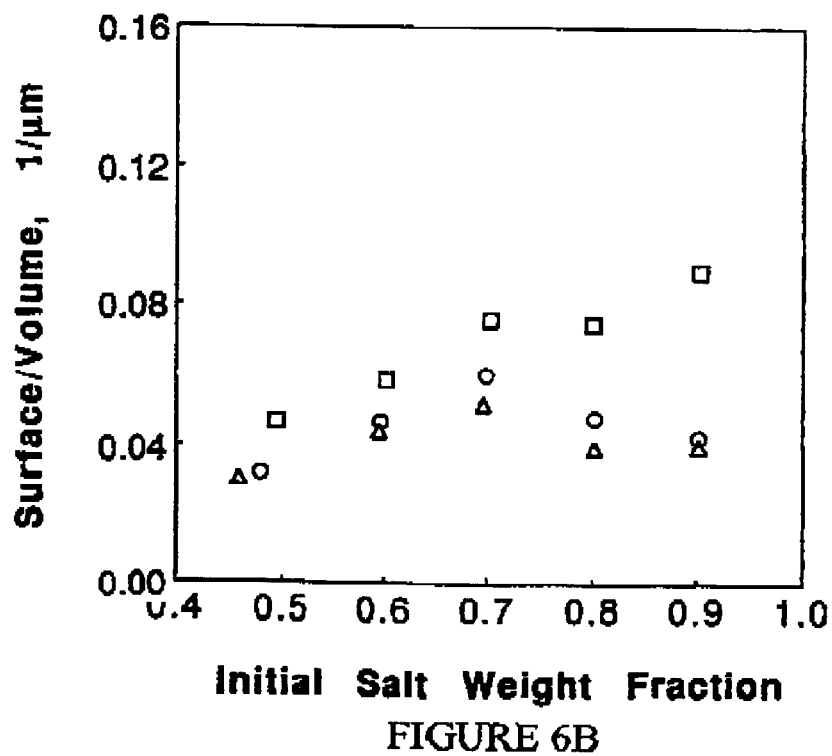

Poly(L-actic acid) (PLLA) porous membranes were prepared with sodium chloride, sodium tartrate, and sodium citrate particles, without any heat treatment to determine the effect of the initial salt weight faction and particle size on the porosity, median pore diameter, and surface/volume ratio. The membrane porosity increased monotonically with the initial salt weight fraction, and was independent of the salt particle size, as shown by FIG. 6. By varying the initial sodium chloride weight fraction from 0.5 to 0.9, as shown by FIG. 6A, the porosity of the PLLA membranes increased from 0.45 to 0.93 when salt particles between 0 and 53 microns were used, from 0.48 to 0.92 when salt particles between 53 and 106 microns were used, and from 0.48 to 0.91 when salt particles between 106 and 150 microns were used. A similar dependence was also observed for PLLA membranes prepared with sodium tartrate or sodium citrate particles.

As demonstrated by the examples, the preferred matrix is an amorphous or semicrystalline polymer such as poly(lactic acid-glycolic acid) having a porosity (defined herein as the fraction of void volume) in the range of 50 to 95% and median pore diameter of 100 to 300 microns, more preferably a median pore size between approximately 150 and 250 microns and a porosity between 75 and 95%, which allows vascular ingrowth and the introduction of cells into the matrix without damage to the cells or patient. As used herein, an amorphous polymer is not crystallized; a semicrystallized polymer is where the degree of crystallinity (fraction of mass of crystallites) is less than 100%. In general, the greater the porosity, the faster the rate of ingrowth of capillaries and connective tissue. The rate of ingrowth is also increased by pre-wetting of the matrix with a surfactant or alcohol followed by saline wash. At this time the most preferred embodiment is an amorphous polylactic acid having 90% porosity and 200 micron median pore diameter.

Polymers

Biodegradable, biocompatible polymers that degrade by hydrolysis can provide temporary scaffolding to transplanted cells and by so doing allow the cells to secrete extracellular matrix enabling a completely natural tissue replacement to occur. Their macromolecular structure is selected so that they are completely degraded and eliminated as the need for an artificial support diminishes. Polymer templates for use in cell transplantation must be highly porous with large surface/volume ratios to accommodate a large number of cells. In addition to being biocompatible, they must promote cell adhesion and allow retention of differentiated function of attached cells. The formation of a vascularized bed within the matrix for cell attachment results in an adequate supply of nutrients to transplanted cells which is essential to their maintenance. They must also be resistant to compression and yet semi-flexible to provide adequate support without discomfort within the recipient.

Studies have been performed with poly(vinyl alcohol), although this material demonstrates some of the drawbacks of using non-degradable materials which may cause formation of a fibrous scar or tissue infection.

Examples of useful polymers include poly(lactic acid), poly(glycolic acid), copolymers thereof, polyanhydrides, polyorthoesters, and polyphosphazines. These are all available commercially or can be manufactured by standard techniques.

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, mixtures thereof, and other materials known to those skilled in the art of cell culture.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

In a preferred embodiment, the matrix contains catheters for injection of the cells into the interior of the matrix after implantation and ingrowth of vascular and connective tissue. Catheters formed of medical grade silastic tubing of different diameters and of differing exit ports to allow even distribution of cells throughout the matrix, as described in the following examples, are particularly useful. Other methods can also be used, such as molding into the matrix distribution channels from the exterior into various parts of the interior of the matrix, or direct injection of cells through needles into interconnected pores within the matrix.

Shaping of the Matrix

The matrix is formed by methods such as casting a polymer solution containing salt crystals into a mold, then leaching out the salt crystals after the polymer is hardened, to yield a relatively rigid, non-compressible structure. This method is described in more detail in co-pending application U.S. Ser. No. 08/012,270, filed Feb. 1, 1993, the teachings of which are incorporated herein.

The polymer matrix can be heated after removal of the solvent to decrease or increase the crystallinity of the matrix. Membranes having high crystallinity, i.e., greater than 20%, will be stronger and will therefore degrade slower than matrixes having reduced crystallinity. To obtain matrices with a lower crystallinity and faster rate of degradation after implantation, the salt and polymer mixture is heated at a temperature that will melt the polymer without affecting the particles. Preferably, the mixture is heated at a temperature between 15° C. and 20° C. higher than the melting temperature $T_m$ of the polymer. A temperature approximately 15° C. higher than the polymer melting temperature is most preferred. The mixture is heated for a sufficient amount of time to uniformly melt the polymer. One hour is normally sufficient.

The melted polymer is cooled to room temperature at a predetermined constant rate. The rate of cooling will also affect crystallinity and the rate of biodegradation after implantation. Preferably, the mixture is cooled at a rate of between 5° and 20° C. per minute. The preferred cooling rate for the formation of a membrane for use in liver or cartilage cells transplants is large enough to yield amorphous PLLA matrices. The mixture cooled at the predetermined rate will have the desired degree of crystallinity for the intended use.

As described in more detail below, since many of the useful polymers are hydrophobic, it may be useful in some embodiments to pre-wet the matrix prior to seeding of cells within the matrix. Suitable surfactants include any of the FDA approved surfactants, including polyols, alcohols, and, in some cases, saline.

Sources of Cells

In a preferred embodiment, cells are obtained either from the recipient for autologous transplantation or from a related donor. Cell transplantation can provide an alternative treatment to whole organ transplantation for failing or malfunctioning organs such as liver and pancreas. Because many isolated cell populations can be expanded in vitro using cell culture techniques, only a very small number of donor cells may be needed to prepare an implant. Consequently, the living donor need not sacrifice an entire organ.

Cells can also be obtained from established cell lines which exhibit normal physiological and feedback mechanisms so that they replicate or proliferate only to a desired point.

For gene therapy, gene transfer vectors can be introduced into different cell types, such as endothelial cells and myoblasts, which are transplanted back to the host for the production and local release of proteins and other therapeutic drugs. Methods for gene transfer are well known to those skilled in the art and have been approved by Food and Drug Administration.

Cells types that are suitable for implantation include most epithelial and endothelial cell types, for example, parenchymal cells such as hepatocytes, pancreatic islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, kidney epithelial cells, kidney tubular cells, kidney basement membrane cells, nerve cells, blood vessel cells, cells forming bone and cartilage, and smooth and skeletal muscle.

In one variation of the method using a single matrix for attachment of one or more cell lines, the matrix is configured such that initial cell attachment and growth occur separately within the matrix for each population. Alternatively, a unitary scaffolding may be formed of different materials to optimize attachment of various types of cells at specific locations. Attachment is a function of both the type of cell and matrix composition. Cell attachment and viability can be assessed using scanning electron microscopy, histology, and quantitative assessment with radioisotopes.

Although the presently preferred embodiment is to utilize a single matrix implanted into a host, there are situations where it may be desirable to use more than one matrix, each implanted at the most optimum time for growth of the attached cells to form a functioning three-dimensional organ structure from the different matrices.

The function of the implanted cells, both in vitro as well as in vivo, must be determined. In vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. Studies using labelled glucose as well as studies using protein assays can be performed to quantitate cell mass on the polymer scaffolds. These studies of cell mass can then be correlated with cell functional studies to determine what the appropriate cell mass is. In most cases it is not necessary to completely replace the function of the organ from which the cells are derived, but only to provide supplemental or partial replacement therapy.

Methods of Implantation

The technique described herein can be used for delivery of many different cell types to achieve different tissue structures. For example, islet cells of the pancreas may be delivered in a similar fashion to that specifically used to implant hepatocytes, to achieve glucose regulation by appropriate secretion of insulin to cure diabetes. Other endocrine tissues can also be implanted. The matrix may be implanted in many different areas of the body to suit a particular application. Sites other than the mesentery for hepatocyte injection in implantation include subcutaneous tissue, retroperitoneum, properitoneal space, and intramuscular space.

Implantation into these sites may also be accompanied by portacaval shunting and hepatectomy, using standard surgical procedures. The need for these additional procedures depends on the particular clinical situation in which hepatocyte delivery is necessary. For example, if signals to activate regeneration of hepatocytes are occurring in the patient from his underlying liver disease, no hepatectomy would be necessary. Similarly, if there is significant portosystemic shunting through collateral channels as part of liver disease, no portacaval shunt would be necessary to stimulate regeneration of the graft. In most other applications, there would be no need for portacaval shunting or hepatectomy.

In the following examples, biodegradable polymer foams were prepared and implanted into Fischer rats. The substrates utilized include poly(L-lactic acid) and poly(DL-lactic-co-glycolic acid), which are approved for human clinical use. Though the prevascularization procedure results in the adequate supply of nutrients to attached cells, it also causes the reduction of potential space for transplanted cells. The dynamics of tissue ingrowth and vascularity, and the availability for cell engraftment were determined for a variety of foams to establish their dependence on the polymer composition, structure and morphology. From these studies, the desired biomaterial properties, such as porosity and average pore size, were determined as well as the optimal time for cell injection.

EXAMPLE 1

Preparation of Devices

Materials and Methods

Materials

The homopolymer, poly(L-lactic acid) (PLLA), and the copolymers, poly(DL-lactic-co-glycolic) (PLGA) (85:15) and PLGA (50:50), were supplied by Medisorb (Cincinnati, Ohio). (The ratios 85:15 and 50:50 stand for the copolymer ratio of lactic acid to glycolic acid). The polymer molecular weights were measured by gel permeation chromatography as $M_n$=104,800 ($M_w/M_n$=1.13) for PLLA, as $M_n$=121,100 ($M_w/M_n$=1.16) for PLGA (85:15), and as $M_n$=82,800 ($M_w/M_n$=1.14) for PLGA (50:50) (where $M_n$ is the number average molecular weight and $M_w$ is the weight average molecular weight). Granular sodium chloride (Mallinckrodt, Paris, Ky.) was ground with an analytical mill (model A-10, Tekmar, Cincinnati, Ohio). The ground particles were sieved with ASTM sieves placed on a sieve shaker (model 18480, CSC Scientific, Fairfax, Va.). Chloroform was furnished by Mallinckrodt.

Seven groups of transplantation devices were prepared by a two-step procedure. The devices were made of PLLA, PLGA (85:15), and PLGA (50:50). For PLLA, devices of different porosities, pore sizes, and crystallinities were processed. First, highly porous polymer membranes with desired porosity, pore size, and degree of crystallinity were prepared by solvent-casting and particulate-leaching technique. Briefly, a dispersion of sieved sodium chloride particles in a chloroform solution of PLLA (or PLGA), made by dissolution of the polymer in 8 mL of chloroform, was cast into a 5 cm petri-dish to produce a composite membrane made of polymer and salt particles. The relative amounts of polymer, NaCl, and the size range of sieved NaCl particles for each group are summarized in Table I. By heat treatment, the polymer crystallinity was modified, and the salt particles were leached out to yield a highly porous membrane.

The second step involved lamination of the porous membranes to construct devices with pore structures and morphologies similar to those of the constituent membranes. Each device was comprised of three circular layers of diameter 13.5 mm with a medical grade silicone tubing (0.03 in. inner and 0.065 in. outer diameter; American Scientific Products, McGaw Park, Ill.) inserted in the middle. At a distance of 6.75 mm from the stem of a knot tied at the end of a 5 cm piece of tubing, two 1/16in. rectangular holes were opened facing opposite sides for cell injection. The thicknesses of PLLA, PLGA (85:15), and PLGA (50:50) devices were 4999 (±72), 3531 (±427), and 4484 (±296) μm, respectively. (Averages±s.d. of five measurements). For the devices made of PLLA and reported in Table I, no variation of the thickness with the porosity, pore size, or degree of crystallinity was observed.

The porosity, pore area, surface/volume ratio, and median pore diameter of the porous membranes were measured by mercury intrusion porosimetry, and are presented in Table I. The porosity increased as the initial salt weight fraction increased (by comparing membranes L90e and L80e) and larger pores were formed by utilizing larger salt particles (from L90e and L90c as well as NCL90e and NCL90c).

(The different codes referring to the various membranes are also included in Table I.) From the measurements of porosity and median pore diameter of the above pairs, one infers that though both properties change when either the weight percentage of NaCl or the NaCl particle size is modified, the variation of one of them is more prominent as compared to the other. The degree of crystallinity of the polymers was calculated from the enthalpy of melting which was measured by Differential Scanning Calorimetry (7 Series, Perkin-Elmer Newton Centre, Mass.). The enthalpy of melting of 100% crystallized PLLA used in the calculations was 203.4 J/g.

TABLE I

Preparation Conditions and Properties of Highly-Porous PLLA and PLGA Membranes

| | Preparation Conditions | | | | Membrane Properties | | | |
|---|---|---|---|---|---|---|---|---|
| Polymer | Polymer Mass (g) | NaCl Mass (g) | NaCl wt % | NaCl Range ($\mu m, \mu m$) | Porosity | Pore Area ($cm^2/mg$) | Surface/Volume ($1/\mu m$) | Median Diameter ($\mu m$) | Pore Degree of Crystallinity |
| L90e PLLA | 0.5 | 4.5 | 90 | (250, 500) | 0.83 | 1.39 | 0.030 | 166 | 0.245 |
| L90c PLLA | 0.5 | 4.5 | 90 | (106, 150) | 0.90 | 3.01 | 0.038 | 126 | 0.235 |
| L80e PLLA | 1.0 | 4.0 | 80 | (250, 500) | 0.75 | 1.37 | 0.043 | 137 | 0.245 |
| NCL90e PLLA | 0.5 | 4.5 | 90 | (250, 500) | 0.87 | 1.75 | 0.028 | 179 | 0 |
| NCL90c PLLA | 0.5 | 4.5 | 90 | (106, 150) | 0.89 | 3.48 | 0.048 | 91 | 0 |
| 85LG90e PLGA (85:15) | 0.5 | 4.5 | 90 | (250, 500) | 0.64 | 1.72 | 0.080 | 41 | 0 |
| 50LG90e PLGA (50:50) | 0.5 | 4.5 | 90 | (250, 500) | 0.84 | 4.93 | 0.106 | 36 | 0 |

The devices were stored in a desiccator under vacuum until use. They were sterilized with ethylene oxide (12 hours exposure followed by 24 hours aeration) before implantation. The sterile devices were implanted either dry or prewet in saline just before use. The prewetting procedure involved dipping of devices in ethanol (100%) for one hour followed by immersion in saline (0.9% NaCl) for at least one hour (all under sterile conditions). Prewetting of PLLA and PLGA transplantation devices was very important in cell seeding via injection.

EXAMPLE 2

Implantation and Harvest of Devices

Implantation into rats.

Devices were implanted in the mesentery of male syngeneic Fischer 344 rats (Charles River, Wilmington, Mass.). In a typical experiment, the rat was anesthetized using methoxyflurane (Pitman Moore, Mundelein, Ill.) and its abdominal wall was incised. The mesentery, which is a thin fatty layer of tissue supplying blood to the small bowel, was displayed on sterile gauze carefully to avoid traumatizing the blood vessels or the tissue. The sterile device was placed onto the unfolded mesentery. Then, the mesentery was folded back over the device so as to envelope it, and put back into the rat. The device was sutured on the mesentery using non-absorbable surgical suture (Prolene, Ethicon, Sommerville, N.J.). The laparectomy was closed separately for the muscle layer and the skin with a synthetic absorbable suture (Polyglactin 910, Ethicon). Two devices were implanted in each 200 g rat, one proximally and one distally.

For each parameter tested, a device was harvested after 5, 10, 15, 20, 25, and 35 days, rinsed and stored in a 10% neutral buffered formalin solution (Sigma, St. Louis, Mo.) until sectioning and staining. Samples were sliced into thin sections at half distance from the center line parallel to the tubing and were stained with hematoxylin and eosin (H&E) which allowed for visualization of cells and cell nuclei.

Image Analysis

Figure 1A:
FIGS. 1a, b, c, and d are digitized images of cross sections of semicrystalline PLLA (L90c) transplantation devices harvested at 5, 15, 25, and 35 days. The shadowed area defines the region which was partially filled with ingrowing tissue.
Figure 1B:
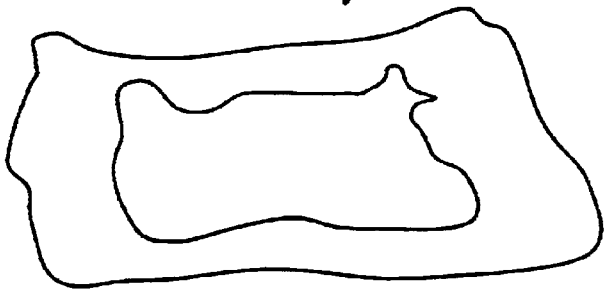
Figure 1C:
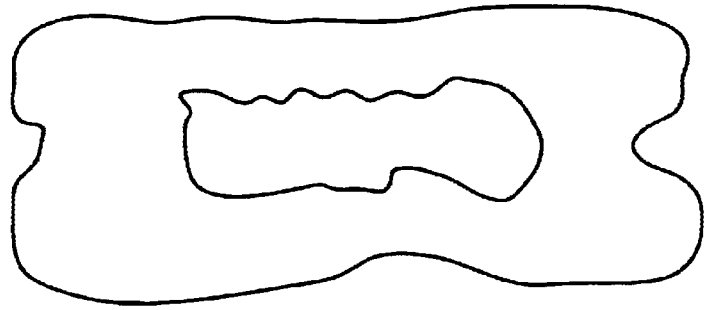
Figure 1D:
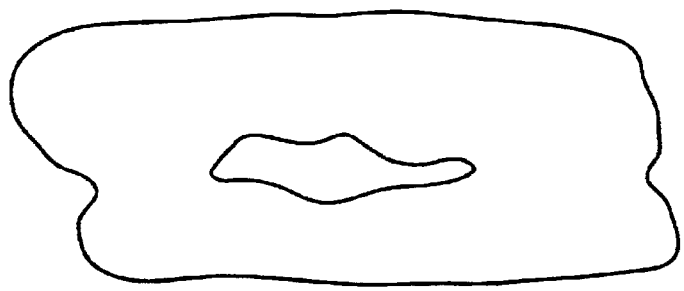
Figure 2B:
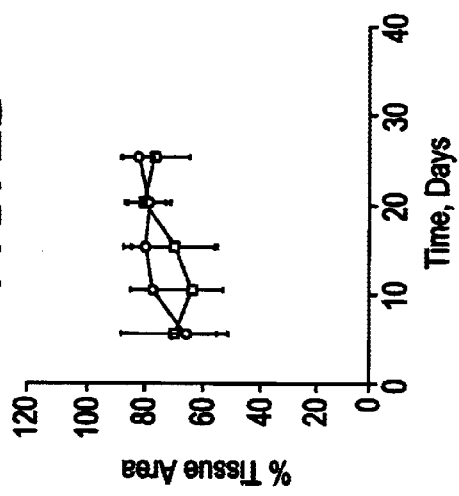
FIGS. 2a, 2b, 2c, and 2d, are graphs of the normalized tissue ingrowth (FIG. 2a), fraction of tissue area of prevascularized regions (FIG. 2b), number of capillaries per field (FIG. 2c), and average capillary area ($\mu m^2$) (FIG. 2d), as a function of implantation time (days), for prewet semicrystalline PLLA (L90e) devices implanted in the distal (n) and proximal site (l) of the mesentery. The error bars for the tissue ingrowth designate averages±range of two experiments whereas those for the tissue area, the number of capillaries, and the average capillary area stand for averages±standard deviation of three 1×1 mm² fields of the same histological section.
Figure 2D:
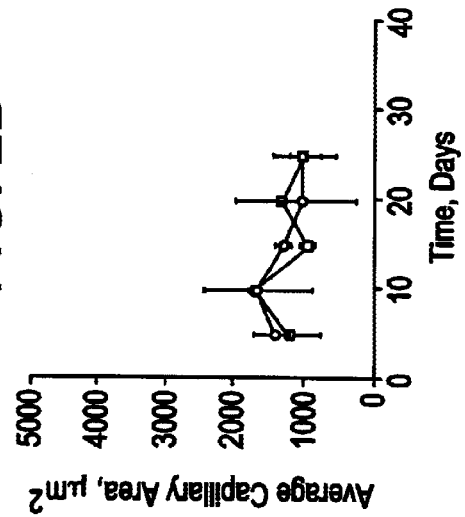
Figure 2A:
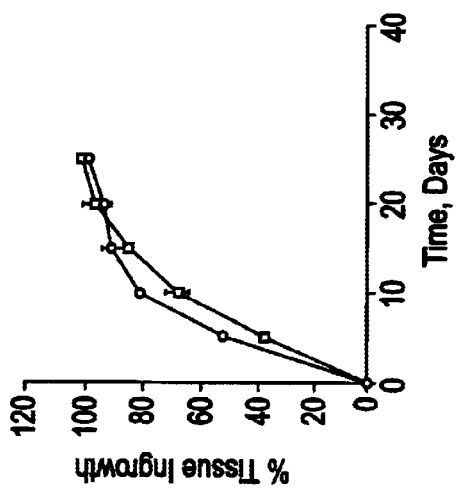
Figure 2C:
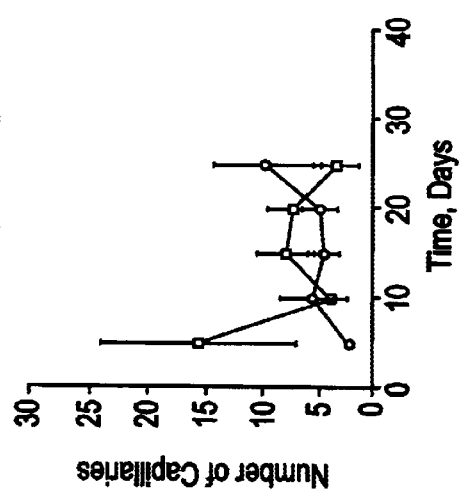
Figure 4B:
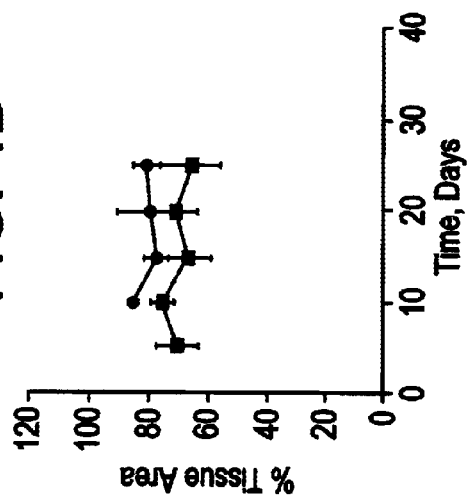
FIGS. 4a, 4b, 4c, and 4d, are graphs of the normalized tissue ingrowth (FIG. 4a), fraction of tissue area of prevascularized regions (FIG. 4b), number of capillaries per field (FIG. 4c), and average capillary area ($\mu m^2$) (FIG. 4d), as a function of implantation time (days), for amorphous PLLA devices of different pore sizes [NCL90e (n) and NCL90c (l)] implanted in a dry form. The error bars for the tissue ingrowth designate averages±range of two experiments whereas those for the tissue area, the number of capillaries, and the average capillary area stand for averages +standard deviation of three 1×1 mm² fields of the same histological section.
Figure 4D:
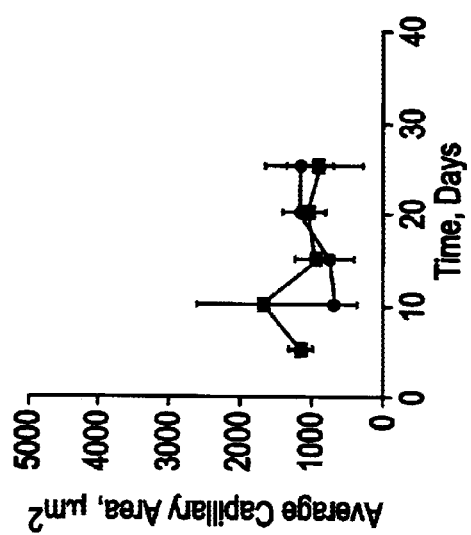
Figure 4A:
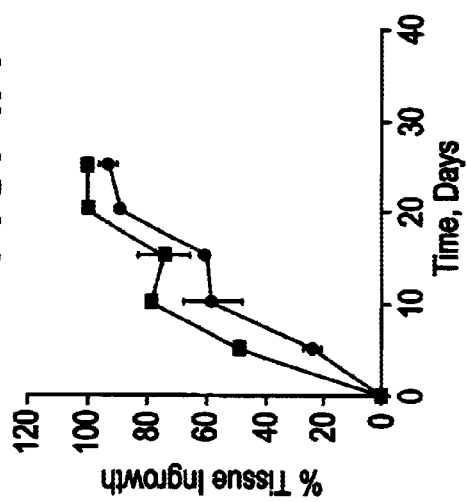
Figure 4C:
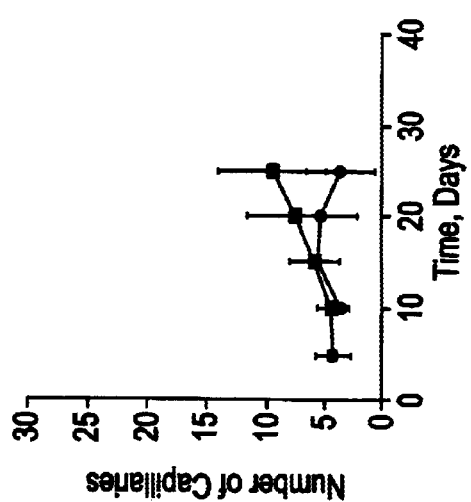

Image analysis was performed with a Megiscan 2 Image Analysis System (Joyce-Loebl, Tyne & Wear, England) equipped with a Polaroid MP-4 Land Camera. From each histological section, the area the tissue had advanced was measured and compared to the total area of the cross section. The area filled by tissue was selected as the area confined between the perimeter of the harvested device and the front of the advanced tissue. A series of actual digitized sections of PLLA (with membrane code L90c as designated in Table I) devices harvested at 5, 15, 25, and 35 days is shown in FIGS. 1a, b, c, and d, respectively. The tissue ingrowth defined by equation (1) provided an estimate of the extent of tissue invasion within the device.

$$\text{Tissue Ingrowth} = \frac{\text{Area Filled by Tissue}}{\text{Total Area}} (100\%)$$

For each harvested device, the tissue ingrowth was determined from the two parallel and symmetric sections, and the average (±range) was calculated. From the variation of tissue ingrowth with implantation time, the optimal time for cell injection was determined, also referred to as prevascularization time (i.e., the time corresponding to 100% tissue ingrowth).

The regions occupied by tissue were not necessarily filled completely. From fields of 1×1 $mm^2$ outside the tissue front, the fraction of tissue area was determined. The tissue area was measured but not the void area because the image of the stained polymer could not be distinguished from that of the vacant area. The percentage of void volume within vascularized regions was calculated as $$\% \text{ Void Volume} = \% \text{ Porosity} - \% \text{ Tissue Area} \qquad (2)$$

The percentage of tissue area provides a very good estimate of the device volume fraction occupied by tissue. Furthermore, the frequency and size of the invaded blood vessels were quantified. All the capillaries within the same field were enumerated and their area determined. The average capillary area was calculated for each field. Three fields from the same section were used to calculate averages (±standard deviation) of the percentage of tissue area, the number of capillaries, and the capillary area.

Results and Discussion

For all the implants harvested, no delamination of the three-layered devices was visually detected from the histological sections. Also, no fibrous capsule was revealed around the catheter that could have hindered the injection of cells into prevascularized devices.

PLLA Devices with 83% Porosity and 166 μm Pore Size.

The tissue ingrowth was first studied for PLLA devices of 83% porosity and 166 μm median pore diameter (L90e) which were prewet with saline, and implanted in the proximal and distal site of the mesentery for a period of 25 days. From FIGS. 2a–d, one infers that the rate of tissue ingrowth was reproducible and independent of the device position in the mesentery. It was observed that PLLA devices 5 mm thick were prevascularized after days. The fibrovascular tissue grew into the devices from the bases and sides. The percentage of tissue area measured from histological sections increased from 67% (average of the values reported in FIGS. 2a–d for devices implanted distally and proximally in the mesentery) at day 5 to 79% at day 25. The corresponding void fractions for cell engraftment were estimated using equation (2) as 16% at day 5 and 4% at day 25.

Effect of prewetting

The tissue ingrowth was dependent on the prewetting of the devices. Although the same devices implanted dry were also prevascularized after 25 days, as shown by FIGS. 3a, b, c and d, the initial rate of tissue induction was much faster for prewet devices. For example, after 5 days of implantation, for prewet devices, the average tissue ingrowth of the measured values for distal and proximal implantation was 44% as compared to only 26% for the dry devices. Also, after 10 days, the relative values of tissue ingrowth were 74% and 44% for prewet and dry devices, respectively. Because the polymer is very hydrophobic, one infers that prewetting reduces the adherence of the ingrowing tissue to the polymer substrate. However, no effect was found on the total tissue area for prevascularized devices, only on the rate. The same low percentage of 4% of void volume was recorded after 25 days of implantation of dry devices. In both cases, the ingrowing tissue was highly vascularized and an appreciable increase of the tissue vascularity with the implantation time was observed. For devices implanted dry, the average number of capillaries was measured as 10.0 (±5.7) at day 5 and as 17.7 (±4.6) at day 35 per field of 1×1 mm$^2$. The average capillary area was calculated as 1100 (±610) μm$^2$ at day 5 and as 1500 (±380) μm$^2$ at day 35.

A fraction of 4% of device volume available for cell engraftment after prevascularization is very small for an efficient transplantation of sufficient cell mass for functional replacement. However, even if the number of cells fitted in the crevices between the polymer and the tissue could supplement organ function, it is very difficult to inject that number of cells without any damage to the cells due to high shear stresses developed at their surfaces as they pass through small pores.

PLLA Devices with 75% Porosity and 137 μm Pore Size.

The dynamics of tissue ingrowth into semicrystalline PLLA devices depended on device porosity and pore size as deduced from the histology studies up to 35 days, as shown by FIGS. 3a–d. For high porosity values, the tissue advanced into the device much faster. After 25 days, devices of 83% porosity (L90e) were prevascularized, whereas those of 75% porosity (L80e) showed a 74 (±12) % tissue ingrowth. The initial thicknesses of the devices were the same. Also, the rate of tissue ingrowth was slower for devices with smaller pores.

PLLA Devices with 90% Porosity and 126 μm Pore Size.

PLLA devices of median pore diameter of 126 μm and porosity of 90% (L90c) exhibited an 85 (±1) % tissue ingrowth after 25 days. The ingrowing tissue was highly vascularized, as indicated by the measured values of capillary frequency and average size over a time period of 35 days. The decreased numbers of capillaries for devices of low porosity (see FIG. 3c for L80e) do not correspond to reduced vascularity of the ingrowing tissue. Rather, because the skeletal polymer volume increases as the foam porosity decreases, they are artifacts due to the field definition that also includes the space occupied by polymer. The same rationale also explains the lower values of the percentage tissue area for the same devices.

Effect of Using Amorphous Versus Semicrystalline Devices.

Much faster tissue ingrowth occurred for amorphous PLLA devices than for semicrystalline ones, as shown by FIGS. 4a–d. Amorphous PLLA devices of 87% porosity and median pore diameter of 179 μm (NCL90e) were prevascularized after 20 days. Here, as for semicrystalline devices, the tissue advanced much faster into devices with larger pore diameters. For devices of similar porosity of 89% and median pore diameter of 91 μm (NCL90c), a tissue ingrowth of 88 (±2) % was measured at the same time. The percentage of tissue area for amorphous PLLA decreased as the foam pore diameter increased. After 25 days of implantation, the ingrowing tissue filled 66 (±10) % of the NCL90e devices and 81 (±4) % of the NCL90c ones, resulting in percentages of void volume for cell transplantation of 21% and 8%, respectively. The tissue vascularity was also consistent. An average number of 9.0 (±4.5) capillaries per field with an average cross-sectional area of 845 (±593) μm$^2$ was measured for NCL90e devices after 25 days. This value corresponds to 13.6 capillaries per mm$^2$ of tissue, which is comparable to the number determined for the L90e devices.

The existence of sufficient space for cell engraftment renders amorphous PLLA devices of high porosity with large pores potential candidates for use as templates for tissue regeneration. Provided that PLLA foams with degrees of crystallinity in the range from 0 to 24.5% prepared using the same relative amounts of polymer and sieved salt particles have similar pore morphologies, as indicated from the mercury porosimetry measurements, one infers that the lower values of tissue area for amorphous PLLA as compared to semicrystalline PLLA reflect different cell-polymer interactions that are not clear yet and need to be explored.

Figure 5:
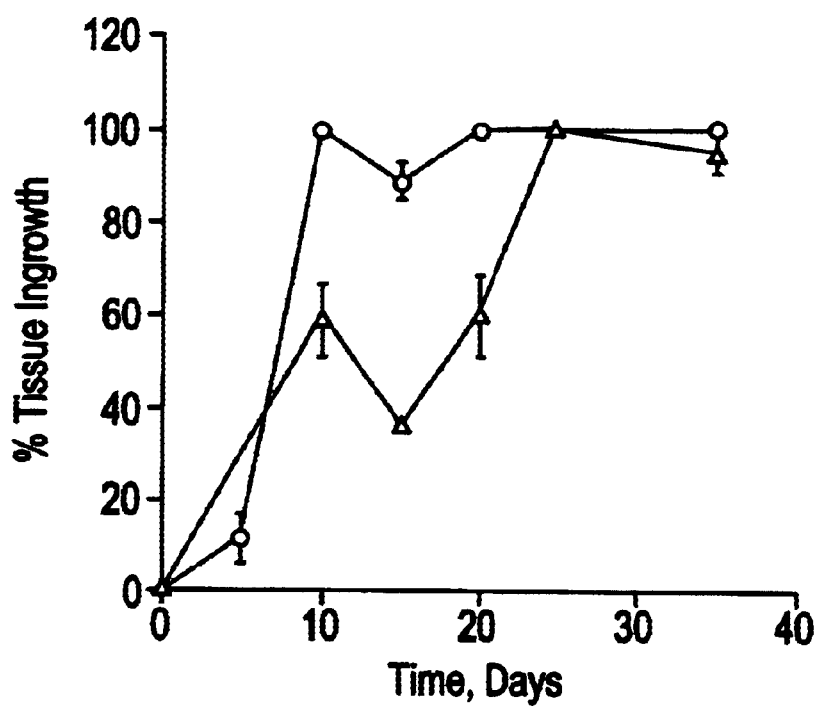
FIG. 5 is a graph of the percent normalized tissue ingrowth as a function of implantation time (days) for PLGA (85:15) (85LG90e) (l) and PLGA (50:50) (50LG90e) (s) devices implanted in a dry form. The error bars designate averages±range of two experiments.

The prevascularization of devices made of PLGA (85:15) and PLGA (50:50) was also studied. The variation of tissue ingrowth with time is shown in FIG. 5. PLGA (85:15) devices were prevascularized after 10 days, whereas for PLGA (50:50), tissue filled the interior of the devices in 25 days. No direct comparison can be made between each other and with PLLA devices because they not only had different pore morphologies (see Table I) but also different thickness. In addition to other possible effects, PLGA (85:15) devices were filled much faster than PLGA (50:50) ones because they were 953 μm thinner. The vascularity of the tissue for both copolymers was consistent and similar to that observed for the PLLA devices.

In conclusion, the data demonstrates that biodegradable polymer foams of appropriate structure and morphology can be vascularized and provide a substrate for cell attachment and growth.

Although this invention has been described with reference to specific embodiments, variations and modifications of the method and means for constructing artificial organs by culturing cells on matrices having maximized surface area and exposure to the surrounding nutrient-containing environment will be apparent to those skilled in the art. Such modifications and variations are intended to come within the scope of the appended claims.

We claim:

1. A polymeric matrix formed of a biodegradable, biocompatible, synthetic, amorphous polymer or semi-crystalline polymer with a degree of crystallinity in the range of from 0 to 24.5% having a porosity of between 45 to 93% and a pore size range of greater than zero to 500 microns that is suitable for attachment and proliferation of dissociated cells.

2. The matrix of claim 1, wherein the biodegradable polymer is selected from the group consisting of polyanhydrides, polyorthoesters, polyglycolic acid, polylactic acid, copolymers and blends thereof.

3. The matrix of claim 1, wherein the polymer is an amorphous polymer.

4. The matrix of claim 1, wherein the polymer is a semi-crystalline polymer.

5. The matrix of claim 1, further comprising a catheter for introducing cells into the interior pores of the matrix after implantation.

6. The matrix of claim 1, wherein the median pore diameter is up to 150 microns.

7. The matrix of claim 1, further comprising a wetting agent.

* * * * *